United States Patent [19]

Pujals, Jr.

[11] Patent Number: 4,854,306
[45] Date of Patent: * Aug. 8, 1989

[54] CERVICAL/OCCIPITAL SUPPORT

[76] Inventor: Charles Pujals, Jr., 119 Fayette St., Bridgeton, N.J. 08302

[*] Notice: The portion of the term of this patent subsequent to Jan. 7, 2003 has been disclaimed.

[21] Appl. No.: 121,787

[22] Filed: Nov. 16, 1987

Related U.S. Application Data

[63] Continuation-in-part of Ser. No. 816,883, Jan. 7, 1986, Pat. No. 4,708,129, which is a continuation-in-part of Ser. No. 563,160, Dec. 19, 1983, Pat. No. 4,562,833.

[51] Int. Cl.$^4$ .......................... A61F 5/01; A61F 5/04
[52] U.S. Cl. .................................... 128/75; 128/76 R; 128/DIG. 23; 128/87 B
[58] Field of Search .................. 128/75, 76 R, 84 R, 128/84 C, 87 B, 89 A, DIG. 23

[56] References Cited

U.S. PATENT DOCUMENTS

| Re. 32,219 | 8/1986 | Garth | 128/87 B |
|---|---|---|---|
| 2,674,996 | 4/1954 | Stowell et al. | 128/75 |
| 2,818,063 | 12/1957 | Smith et al. | 128/87 |
| 3,320,950 | 5/1967 | McElvenny | 128/75 |
| 3,522,804 | 5/1968 | Towbin | 128/DIG. 23 |
| 3,756,226 | 9/1973 | Calabrese et al. | 128/75 |
| 3,850,164 | 11/1974 | Hare | 128/DIG. 23 |
| 3,921,626 | 11/1975 | Noel | 128/DIG. 23 |
| 4,034,747 | 7/1977 | Leroy | 128/DIG. 23 |
| 4,161,946 | 7/1979 | Zuesse | 128/87 B |
| 4,211,218 | 7/1980 | Kendrick | 128/87 R |
| 4,232,663 | 11/1980 | Newton | 128/DIG. 23 |
| 4,538,597 | 9/1985 | Lerman | 128/75 |
| 4,543,947 | 10/1985 | Blackstone | 128/75 |
| 4,589,407 | 5/1986 | Koledin et al. | 128/87 |
| 4,657,003 | 4/1987 | Wirtz | 128/89 R |
| 4,702,233 | 10/1987 | Omizioli | 128/DIG. 23 |
| 4,745,922 | 5/1988 | Taylor | 128/DIG. 23 |

FOREIGN PATENT DOCUMENTS 2404683  8/1975  Fed. Rep. of Germany ........ 128/75

Primary Examiner—Edgar S. Burr
Assistant Examiner—Tonya Lamb

[57] ABSTRACT

A support is provided for a user's head and neck which provides varying degrees of support depending on the combination of support members utilized. A posterior shell which supports the occiput can be combined with either ear protectors or an anterior shell, or both and an overlying posterior shell can be utilized to provide increased support. A single posterior shell could include all support features such as the ear protectors formed as an integral port thereof. The anterior shell can have molded contours to increase its rigidity and jaw engaging side walls to reduce lateral movement.

22 Claims, 9 Drawing Sheets

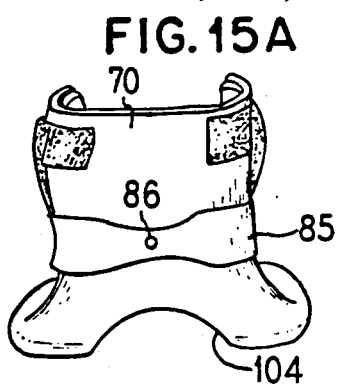
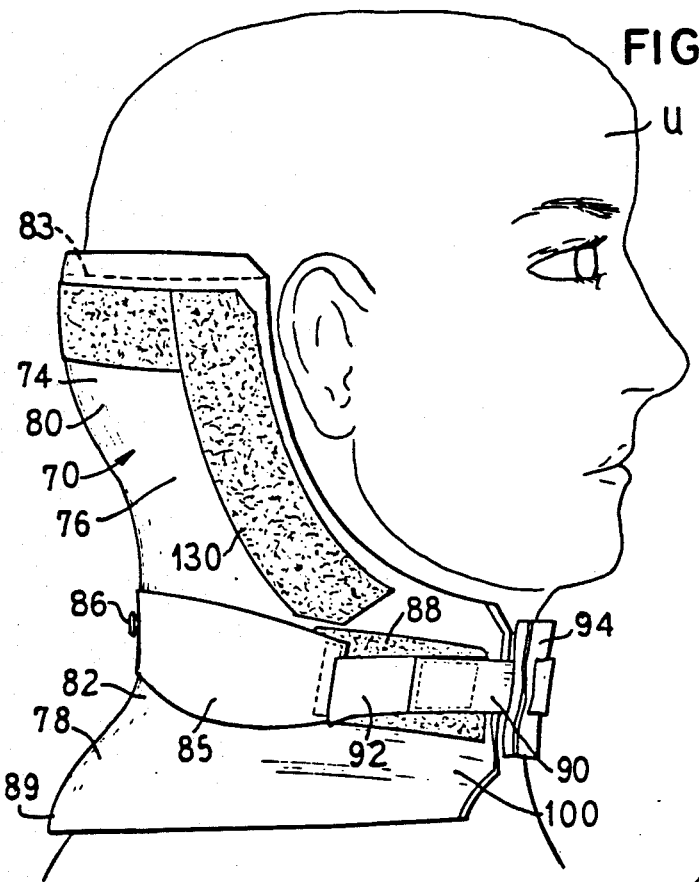
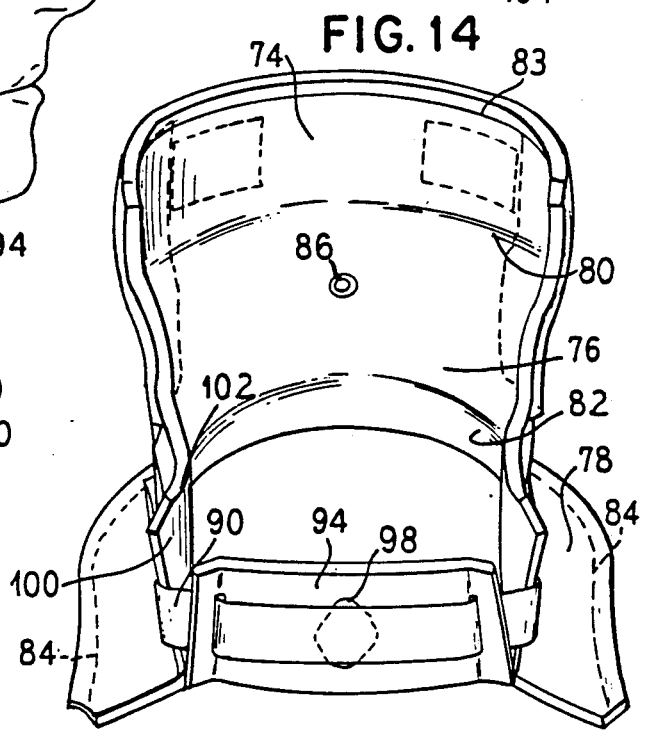
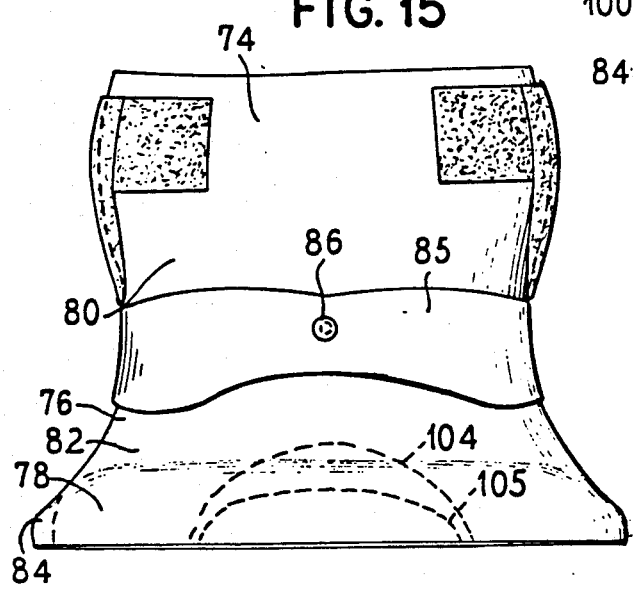
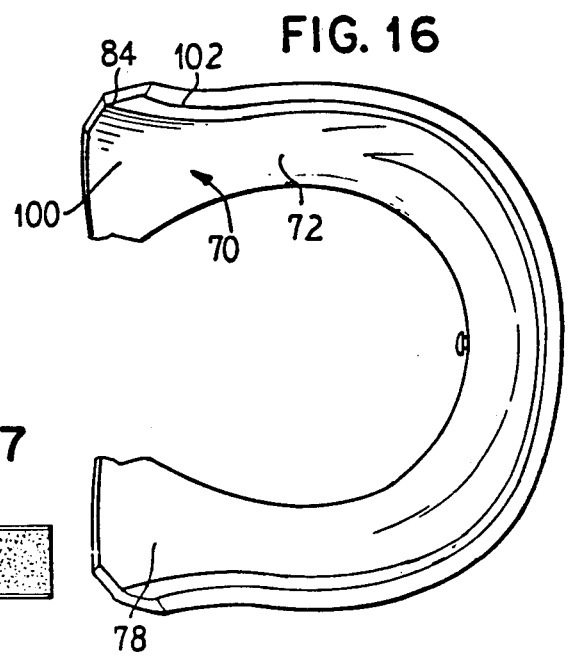
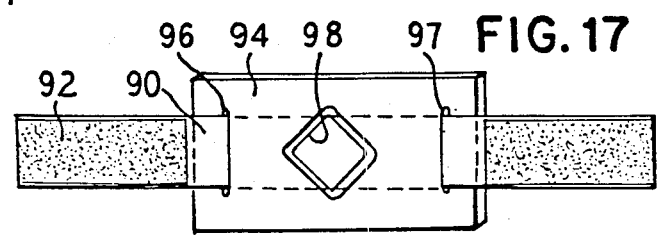

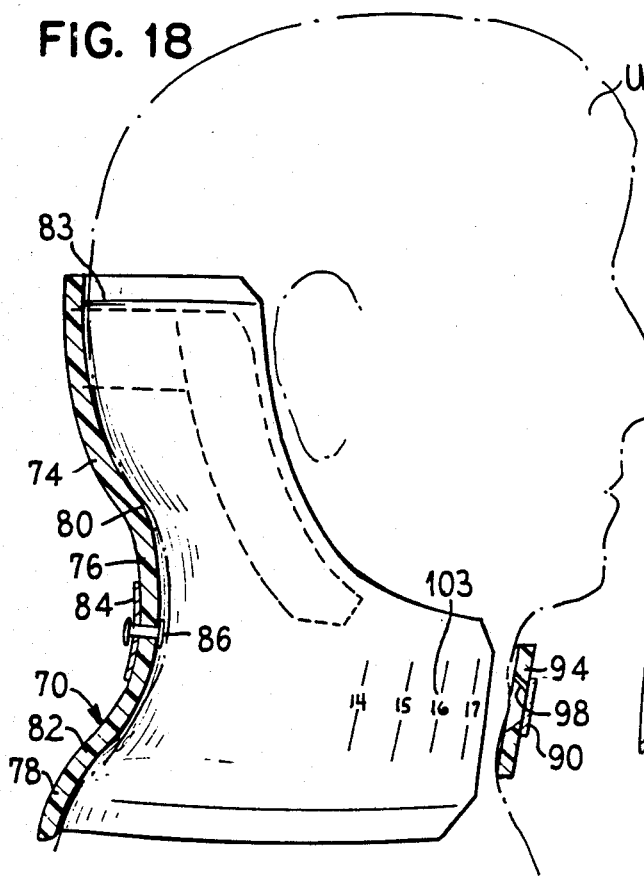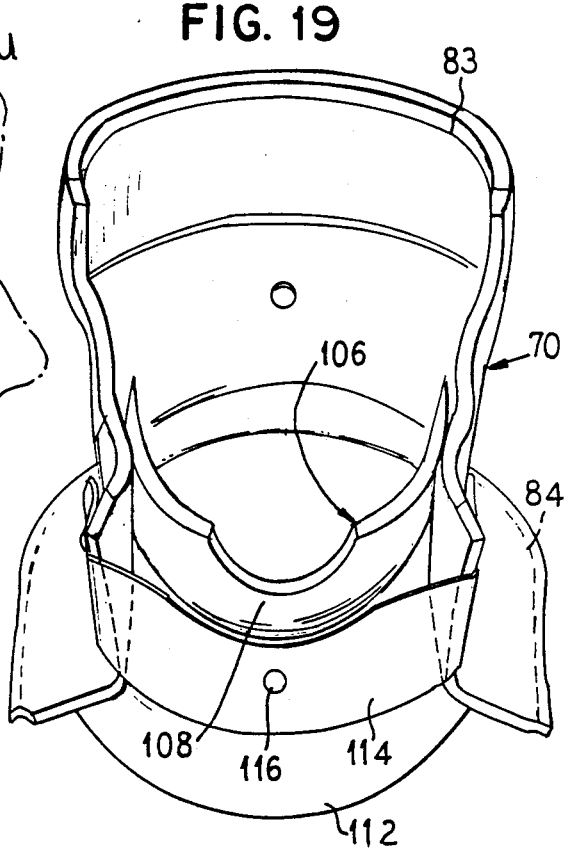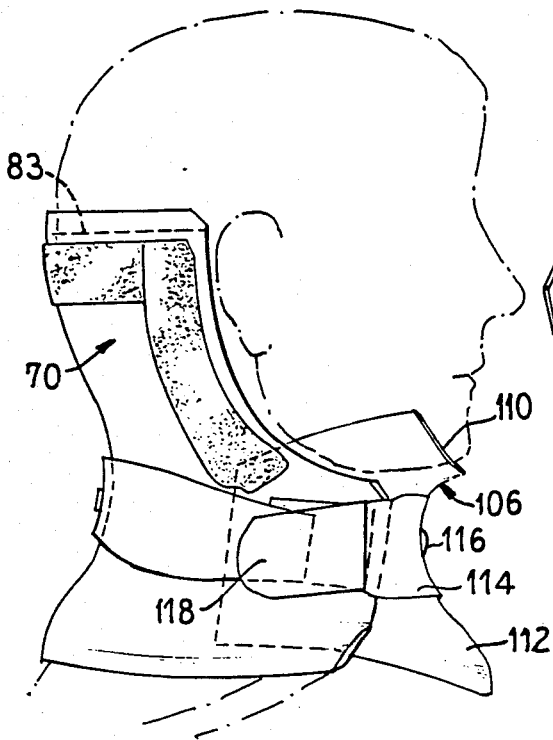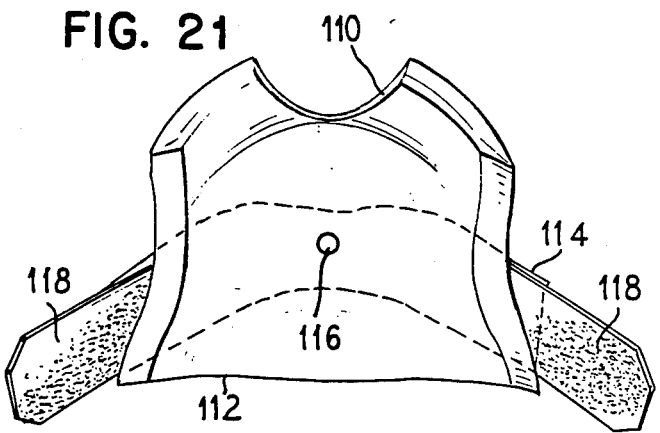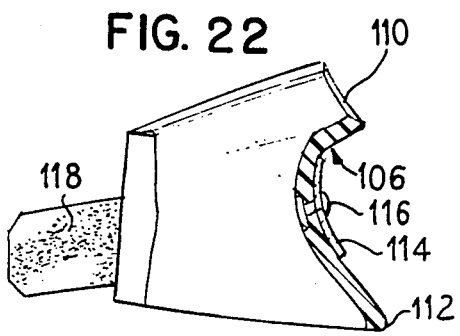

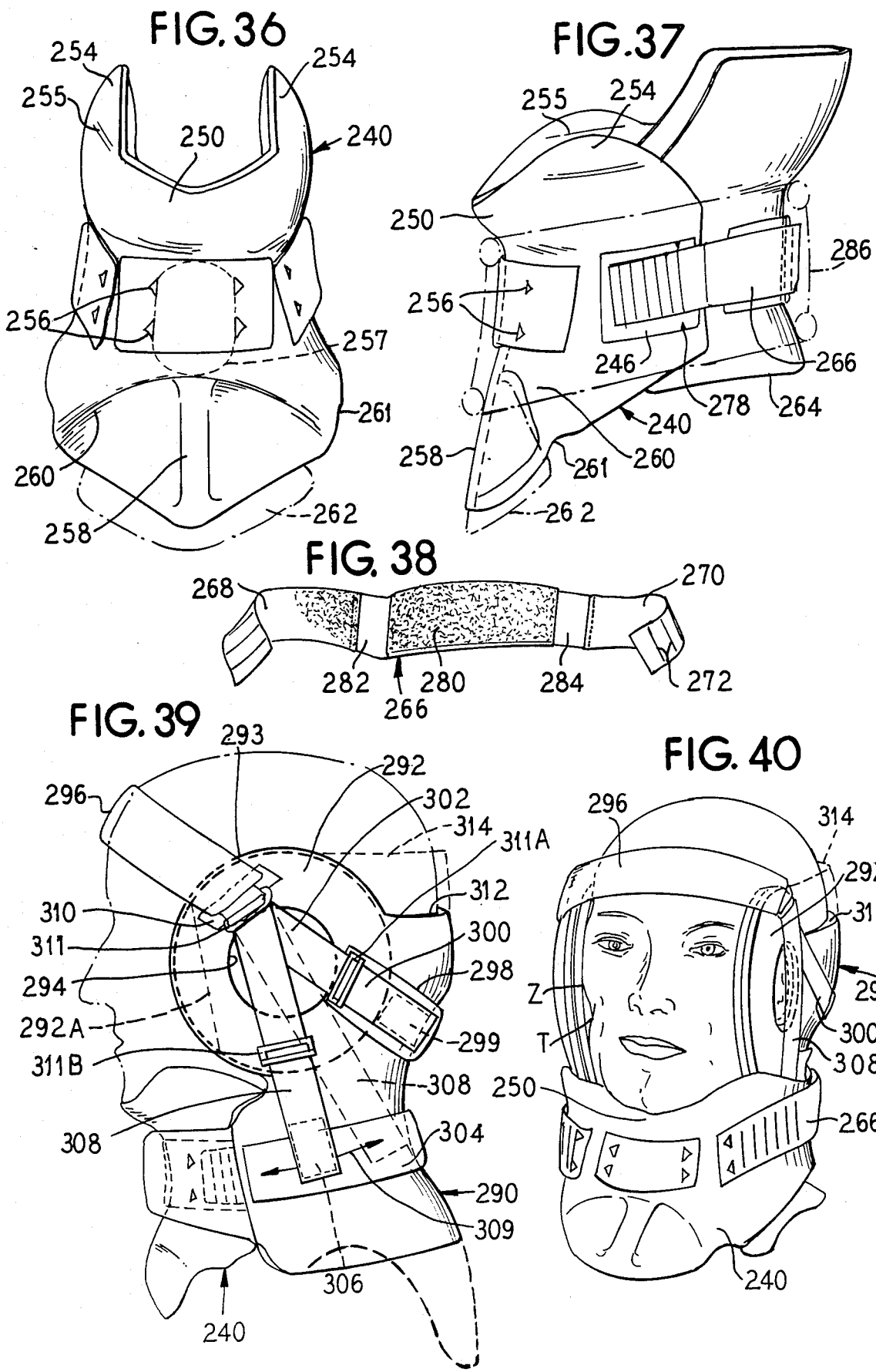

CERVICAL/OCCIPITAL SUPPORT

BACKGROUND OF THE INVENTION

This application is a continuation-in-part of my pending U.S. patent application Ser. No. 816,883 filed Jan. 7, 1986 now issued as U.S. Pat. No. 4,708,129 which was a continuation-in-part of my U.S. patent application Ser. No. 563,160 filed Dec. 19, 1983 and now issued as U.S. Pat. No. 4,562,833.

FIELD OF THE INVENTION

The present invention relates to cervical orthopedic devices and more particularly to a semi-rigid neck brace providing anterior, posterior and lateral support.

DESCRIPTION OF THE PRIOR ART

There are presently available several different types of cervical collars or neck braces which are used in the treatment and therapy of cervical trauma. The major problem with fitting foam cervical collars is that there is not adequate support to the neck and skull posteriorly. Various posterior supports have been attempted, but failed to fulfill their purpose of comfortable support. This failure often produces increased muscular tension type headaches, loss of sleep, increased myalgia (muscular aches and pains) and poor posture.

The presently available collars such as those disclosed in U.S. Pat. Nos. 3,285,243; 3,756,226 and 4,205,667, that do support the head and neck are too limiting and do not allow enough movement to compensate for postural changes. These previous collars are too restrictive causing them to be uncomfortable to wear or tolerate. They fulfill the need for early firm support to limit motion, to prevent further injury of acute trauma or post-operatively, although they do not prevent lateral or rotational head and neck movement. These collars lose some of the support with a decrease in muscle spasm which requires refitting to provide accurate support. These collars generally do not provide support in an ideal position and are not properly anatomically adapted to provide a comfortable restriction against movement or supporting quality without excessive pressure on the neck or chin. Another disadvantage is the spacing of the support away from the skin. The device disclosed in U.S. Pat. No. 3,285,243 does have skin contact limited to the mid-line area of the interscapular area to the basal area of the skull.

These collars are rigid devices to give support, restrict motion and to allow rest to promote healing. Rigid supports have disadvantages in that they increase spasm, decrease blood flow because of the over activity of muscles, cause swelling of synovial joints in the cervical spine, cause cervical muscle weakness because of restricted motion in injury, are difficult to get proper support for all patients, and do not fit to the skin.

SUMMARY OF THE INVENTION

The present invention provides for a neck brace or support which combines the collar-brace concept. It is a semi-rigid polymeric plastic material such as PLASTAZOATE or VOLARA shell contoured to fit the occipital area of the skull and neck posterolaterally to the base of the neck. The addition of controlled recovery foam polyurethane such as COMFORM ® foam or TEMPER foam assures comfort, adequate fit, and support while allowing postural changes. By allowing these postural changes, there is the advantage of improving the function of joint mechano-receptors and muscles which will decrease spasm and increase blood flow of the involved area.

Adequate support of the head and neck is needed for several reasons. One reason is to unload the skull from the cervical spine without excessive restriction of motion. Secondly, it is important for the body to move enough to maintain muscle function and reduce spasm, reduce swelling, and increase blood flow leading to decreased swelling. Also, the joint mechano-receptor activity via active/passive movement gives greater muscle function for balance around joints, gives support to the skull and improves posture.

The brace-support of the present invention has a tight fit increasing support to the injured muscles and joints, increasing relaxation to injured muscles and joints, and substitutes for muscle function, thereby increasing healing, blood flow and reducing swelling. It decreases nervous system activity, especially muscle spasm, via pressure on the skin mechano-receptors resulting in accomodation leading to decreased muscle tone.

The present neck brace has a U-shaped body construction which follows various contours. It follows the contour of the occiput between the ears usually $\frac{1}{2}$-$\frac{3}{4}$" away from the attachment of the ears to the skull, thereby cradling the posterior skull. The U-shaped body also follows the contour of the atlanto-occipital junction attachment of the neck to the skull. Further, the body follows the contour of the posterior lateral neck from atlanto-occipital junction to the base of the neck at the beginning of shoulder level and could extend to interscapular area.

The various contours of the brace body are purposefully designed to give the necessary support and rigidity without the addition of an extra reinforcing device to the exterior. In one embodiment of the invention the U-shaped body support is held against the occiput and neck by a foam or plastic collar. As the U-shaped circumference is narrowed to follow the contours of the head and neck, it becomes more rigid, thereby supporting the involved structures in the injured area. In other embodiments of the invention, the brace support body is incorporated into a pillow for use in a reclining position, or multiple brace bodies are nested to provide sufficiently rigid support.

The rigidity attained by the brace body does not totally prevent any motion. It is a gentle rigidity that allows forceful movement when position change will bring relief to the user. One of the purposes and objects of this collar is to allow enough movement by the wearer to maintain joint mechano-receptor activity of the cervical apophyseal joints and surrounding muscles. Another purpose and object of the contour fit is to increase the temperature of the supported area. This is accomplished by the close fit of the collar to the skin, thereby dilating the blood vessels. The increased blood flow hastens healing by decreasing muscle spasm and swelling, thereby allowing adequate healing to take place.

Other embodiments of the present invention include continuously adjustable attachment means such as hook and pile (such as VELCRO ® attachment means) straps for holding the brace shell on the user's neck such that the degree of tightness of the shell against the user's neck and head is infinitely adjustable. A special front strap may be utilized which has a recessed area for the larengeal prominence and the front wing portions of the shell may have outwardly directed ends to hold the strap away from the front of the neck to relieve pressure on the user's larynx. The shell may also include a plurality of trim lines on the back of the shell corresponding to the spinal area to improve support in patients with postural deformities such as that caused by arthritis or in kyhphotic patients.

The shell may also be used with other available chin supports as a front attachment to the shell. Also, ear protectors may be utilized which are attachable to the shell by means of hook and pile straps which have a central cut-out portion for receiving the patient's ear and a raised foam ring surrounding the ear which is particularly useful for accident victims who generally have their head restrained during transport from the accident scene to the hospital by means of sand bags placed against the sides of their heads. The ear protectors prevent unnecessary and uncomfortable pressure against the ears caused by the sand bags and allow viewing of the ears to detect bleeding and leakage of spinal fluid. The position of the ear protectors is continuously adjustable by means of the hook and pile straps.

An abbreviated form of the shell is also provided which does not require the bottom portion of the shell which generally rests upon the patient's shoulders. The abbreviated shell can be held in place on the back of the neck by means of a hook and pile attachment to a foam or plastic collar.

Several additional structural arrangements and features are provided to the above described shells to make the shells more effective and easier to use. For example, the shells may be provided with cloth covers to provide a moisture absorbing layer for use with the shells and which can be easily removed for cleaning and replacement.

The ear pads are improved and in one embodiment of the invention the posterior shell includes an integral ear protector portion to provide additional support for the ear pads and skull.

The loop and pile fastening system can be provided with horizontal and vertical markings to make the fitting of the shell to the patient more consistent and easy to measure and duplicate as well as to permit proper adjustment of the shell.

An anterior shell is provided with raised and inwardly curving sides to provide an improved holding of the user's jaw while still permitting sufficient blood flow to the face and head through facial arteries along the jaw line. The interior shell has an open chin cup to accomodate jutting jaws and also includes various reinforcing contours to provide enhanced rigidity of the shell while still permitting limited, deliberate movement by the patient. The anterior shell may be provided with air holes to allow some air movement in the anterior portion of the shell and a soft foam pad is provided on a lower portion for chest pressure relief.

A foam collar with a pointer can be utilized in connection with markings on the hook and pile fastening pads to provide accurate positioning and tightening of the collar and the collar can be permanently secured by rivet or other fastening devices to prevent adjustment by the patient after fitting by the medical personnel.

It is a purpose and object of the present invention to provide adequate support to injured head and neck structures with properly contoured semi-rigid devices that accomodate to structural differences between patients, that control the injured area by anatomical positioning thereby avoiding extra trauma, especially during early acute injury when there is decreased muscle control and, as healing progresses, to permit a decrease in the external support by the device to allow increased controlled movement by the patient. Pain free movement assists the healing process by increasing muscle function and strengthening which results in decreased pain, decreased muscle spasm and increased blood flow. This results in an eventual recovery from the disability being treated. The structural design disclosed provides anatomical support with the use of contoured, semi-rigid shells and accomodates to acute/semi-acute/healing postures by use of the same structural supports. The structural design also permits progressive decrease in support as healing progresses thereby permitting the patient to gradually increase movement. For example the use of a duplicate outer shell with ear pads and head band is much more restrictive and provides much greater support than the use of an anterior and posterior shell combination or, the use of only a posterior shell with a foam collar. As muscle function and strengthening improves, eventual removal of all support will be possible, and the present device accomodates various stages of the path to recovery.

If there is a reoccurrence of discomfort, weakness, etc. then the present device permits the user to resume the simplest support or combination of elements that relieves the symptoms thus enhancing early recovery and comfort. The disclosed device is especially valuable with patients suffering recurring chronic disorders of the head and neck including tension headaches, spains, strains and various sports injuries.

BRIEF DESCRIPTION OF THE DRAWINGS

FIG. 13 is a side elevational view of a head and neck support embodying the principles of the present invention held on by an improved retaining means.

FIG. 14 is a front elevational view of the support shown in FIG. 13.

FIG. 15 is a rear elevational view of the support shown in FIG. 13 also showing trim lines.

FIG. 15A is a rear perspective view of the support shown in FIG. 13 with a rear trim area removed.

FIG. 16 is a bottom elevational view of the support shown in FIG. 13.

FIG. 17 is a rear elevational view of the retaining strap shown in FIG. 13.

FIG. 18 is a side sectional view of the support shown in FIG. 13.

FIG. 19 is a front elevational view of the support of FIG. 13 including a front chin support member.

FIG. 20 is a side elevational view of the head and neck support and chin support of FIG. 19.

FIG. 21 is a rear elevational view of the chin support shown in FIG. 19.

FIG. 22 is a side sectional view of the chin support shown in FIG. 21.

FIG. 36 is a front view of the anterior shell of FIG. 34 with the cover removed.

FIG. 37 is a side elevational view of a combination of the anterior shell of FIG. 36 with a posterior shell.

FIG. 38 is a perspective view of a strap which can be utilized to hold the anterior and posterior shells together.

FIG. 39 is a side elevational view of an alternative embodiment of a posterior shell incorporating ear protectors and a head band.

FIG. 40 is a perspective view of the shell arrangement of FIG. 39.

DESCRIPTION OF THE PREFERRED EMBODIMENTS

Figure 1:
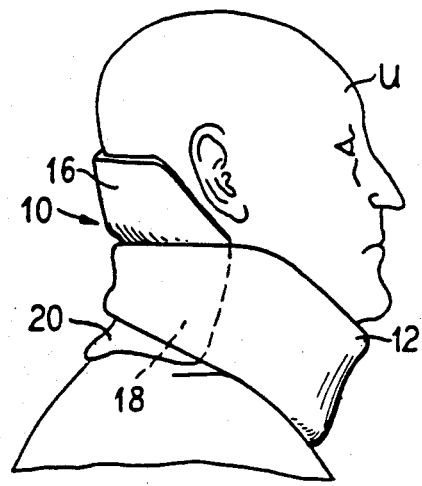
FIG. 1 is a side view of a neck brace embodying the principles of the present invention being worn by a user.
Figure 6:
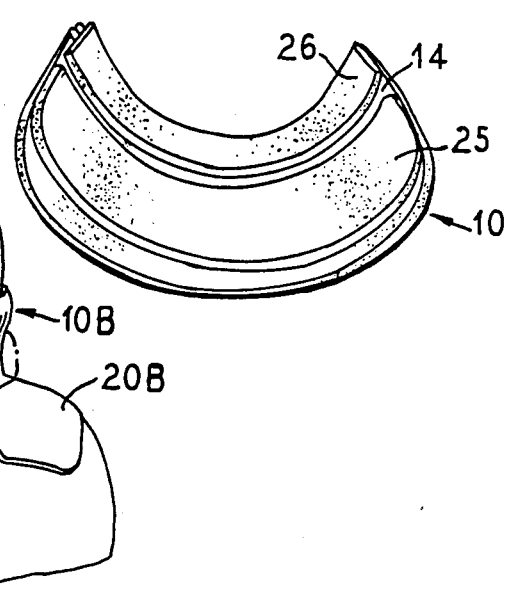
FIG. 6 is a top view of the neck brace of the present invention.

In FIG. 1 there is generally shown a neck brace 10 embodying the principles of the invention which is being worn on the neck of a user U. The brace 10 is held in place by a foam collar 12 which surrounds the user's neck and the brace 10 to hold the brace in close conformity with the posterior region of the user's neck, shoulders and lower skull. As seen in FIG. 6, the brace 10, when viewed from above, is generally U-shaped having an inner-edge or an inner-surface 14 which conforms generally with the posterior neck area of the user. The brace 10 is contoured to provide distinct surface areas for contact with specific anatomical regions of the human body.

Figure 3:
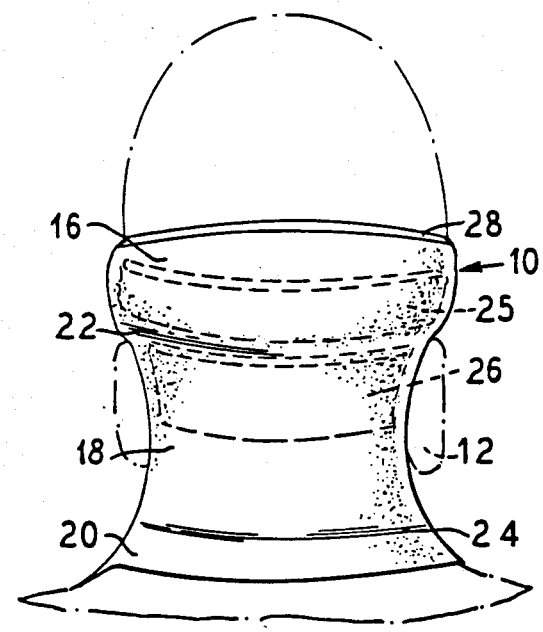
FIG. 3 is a rear elevational view of the brace of FIG. 1.

As seen in FIGS. 1 and 3, an upper surface area 16 provides support and cradles the occiput between the ears. This area also prevents hyper-extension at the atlanto-occipital junction. A second central area 18 surrounds and contacts the posterior neck area and a third lower area 20 contacts and rests on the suprascapular region of the user's shoulders. Transition zones 22 and 24 occur between the first and second areas and the second and third areas respectively.

The brace 10 is constructed of a semi-rigid material such as polymeric plastic material and the various contours of the brace not only give the necessary support but also increase the rigidity of the brace 10. The rigidity of the brace is not so great as to totally prevent any motion. The brace does have some resiliency which allows forceful movement when a position change will give relief to the user.

Figure 2:
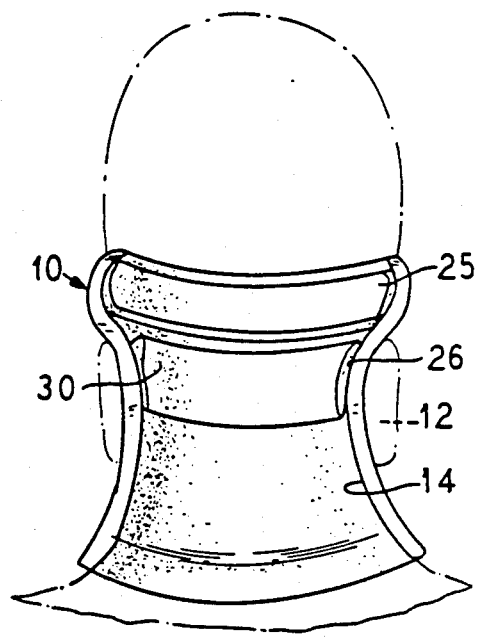
FIG. 2 is a front elevational view of the brace of FIG. 1 showing internal pad locations.
Figure 5:
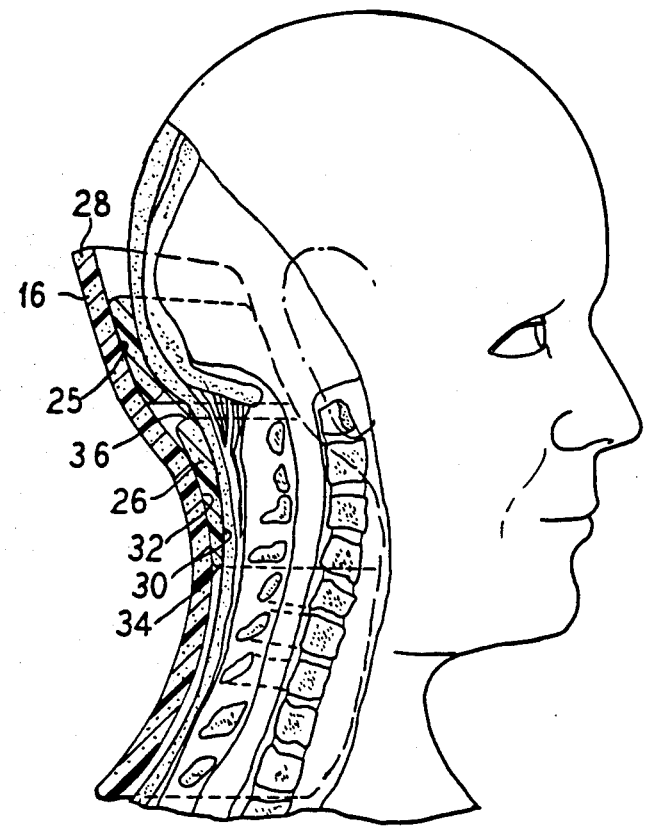
FIG. 5 is a side sectional view of the brace of FIG. 1 and showing a portion of the human anatomy cut away to define the positioning of the brace with respect to the wearer.

In order to increase the comfort of the brace as well as to provide additional support and positive skin contact, one or more foam pads such as those shown at 25 and 26 in FIG. 2 can be supplied on the interior wall 14 of the brace 10. The pads shown in FIGS. 2 and 3 are lateral pads which extend across the width or a portion of the width of the brace 10. The top pad 25 is positioned just below a top end 28 of the brace 10 and is positioned to abut the user's scalp and to overlie the occiput thereby supporting and cradling the occiput. This placement is best seen in FIG. 5 which shows the upper area 16 of the brace with the upper pad 25 positioned laterally just below the top end 28 of the brace 10 and the pad 25 overlying and cradling the occiput.

The second lateral pad 26 is positioned below the top pad 25 and it extends across a portion of the width of the brace 10. The lower pad 26 has a front wall 30 which is at a small angle to a rear wall 32 such that the pad 26 is wedge-shaped with a bottom end 34 being narrower than a top end 36. This wedge-shape more readily conforms to the upper neck and lower skull portion overlying the atlanto-occipital junction in the region of the first through third cervical vertebrae.

The first cervical vertebrae C1 or atlas is a ring-shaped body which is positioned above and receives the odontoid process or dens of the second cervical vertibrae C2 or axis. The neck is comprised of several cervical vertebrae and movement of the neck depends upon the composite movement of all of the vertebrae. Multiple movments of the cervical spine are possible; lateral rotation which is turning the chin to the shoulder occurs mainly between the first and second vertebrae; flexion, which is movement of the chin toward the sternum; extension, which is movement of the occiput backward so that it approximates the cervical spinous process; and lateral bending which is a movement of the ears toward the shoulders while looking straight ahead.

During the treatment and therapy of cervical trauma, it is necessary to immobilize the neck and also to support the head while the injured area heals. In some types of therapy, although the neck is immobilized, some motion is important to allow the body to move enough to maintain muscle function and reduce spasm, reduce swelling and increase blood flow which leads to improved healing. The brace 10 of the present invention provides this limited motion while at the same time providing the restriction and support required in the treatment of the trauma.

Figure 4:
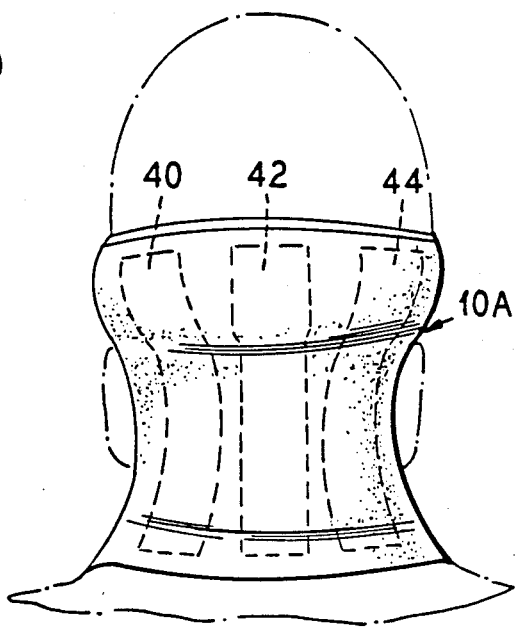
FIG. 4 is a rear elevational view of an alternate embodiment of the brace of FIG. 1.

An alternative embodiment of the brace is shown in FIG. 4 at 10A where it is seen that the body or shell of the brace is virtually identical to that shown in FIGS. 1-3, 5. The difference with the brace in FIG. 4 is that the supporting pads run longitudinally as are indicated by their showing in phantom at 40, 42 and 44. Three longitudinal pads are shown which will provide support at specific areas. The middle pad 42 overlies the posterior portion of the cervical vertebrae and occiput and applies pressure to the vertebrae against the spinous processes of the vertebrae. The left and right lateral pads 40 and 44 apply pressure to and support to the lateral muscles and joint capsules of the vertebrae. The thickness of the lateral pads can be adjusted to further the lateral movement within the brace. The polyurethane foam used for the pads is pliant and resilient and conforms to the contours of the adjoining area, therefore although the bony prominences of the posterior spinous processes have the most pressure applied to them, there is also pressure applied in the depressions between the prominences.

The longitudinal pads are spaced apart which allows for movement and swelling in the neck area. The brace body 10 could be provided with a full foam liner covering the entire interior surface 14 instead of multiple foam strips.

Figure 7:
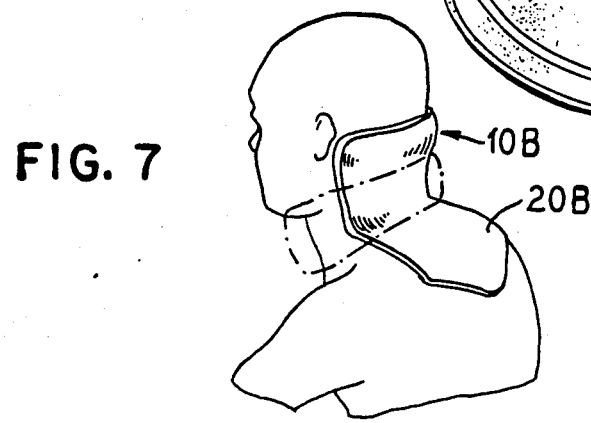
FIG. 7 is a perspective view of an alternative embodiment of the present invention.

A further alternative embodiment is shown in FIG. 7 which shows the brace 10B having a slightly different configuration of the outer shell. In this embodiment, the lower area 20B extends farther onto the suprascapular region of the shoulders and also extends a portion of the way down the vertebra region. This embodiment with the extended lower area 20B provides additional support against extension. This brace 10B, like those described above, can be utilized with the shell alone, or with the lateral, longitudinal or complete padding as described above or a nested shell for increased support as described below.

The thickness of the pads can be selected and adjusted to put the neck into flexion or extension as required.

Figure 8:
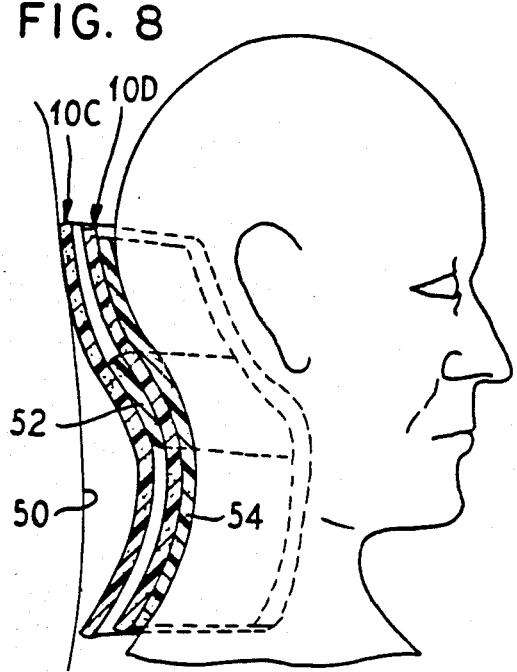
FIG. 8 is a side sectional view of an alternate embodiment of the present invention.

In FIG. 8, there is shown an alternate method of using the neck brace, wherein two brace shells 10C and 10D which are nested, one within the other, to provide additional rigidity to the brace support. The brace can be utilized in this manner when the user is sitting in a substantially upright position such as in a chair with a high back or in an automobile with a head rest and also in a reclining position, for instance in bed, such that the nested braces 10C, 10D are held in place between the user's head and neck and the adjacent surface 50. In the embodiment shown in FIG. 8, a one-piece lateral pad 52 is provided between the two brace shells 10C and 10D.

This pad 52 is placed in the sub-occipital area so that there will be a rocking effect between the shells to increase the adjustability and movement of the shells. A larger one-piece pad 54 covering substantially the entire interior surface of the inner shell 10D is provided to engage the user's head and neck area.

Figure 9:
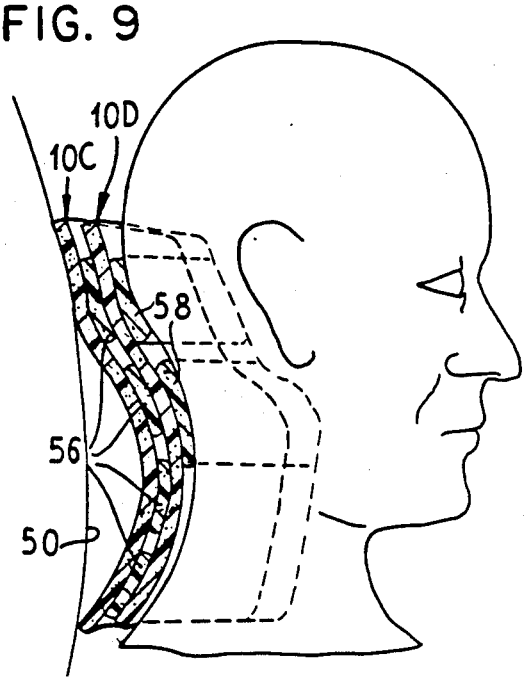
FIG. 9 is a side sectional view of an alternate embodiment of the present invention similar to that shown in FIG. 8.

In FIG. 9, the same nested shells 10C and 10D are provided, but between the two nested shell there are one or more horizontal pad strips 56 and between the inner shell 10D and the user's head and neck there are provided a second plurality of pad strips 58. As described above, these pads may be selectively placed and sized to achieve the desired therapeutic results.

As seen in FIG. 9, the nested shells 10C and 10D may have different lateral dimensions, that is, the inner shell 10D may extend further laterally around the user's neck than the outer shell 10C. In this manner, the outer shell 10C provides the necessary strength and support without detracting from the lateral flexibility provided by the brace.

The use of the brace support shells are shown in FIG. 9 is particularly beneficial when the user is to be seated or reclining in a relatively stationary position for a given period of time. The brace supports provide sufficient support to increase comfort without requiring the confinement and immobility such as when the foam collar is used to secure the brace.

Figure 10:
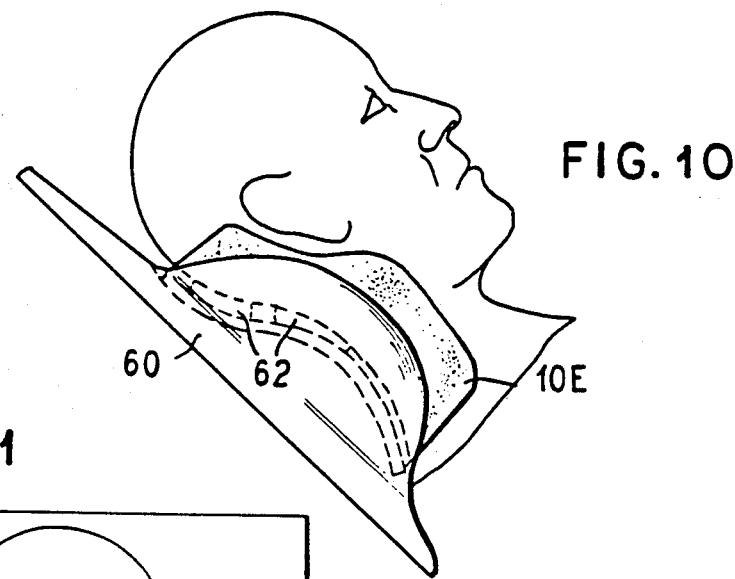
FIG. 10 is a side elevational view of a further alternate embodiment of the present invention.
Figure 11:
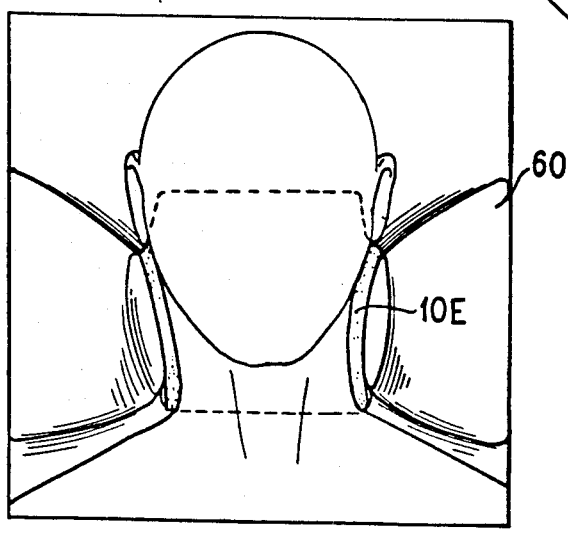
FIG. 11 is a front elevational view of the device shown in FIG. 10.
Figure 12:
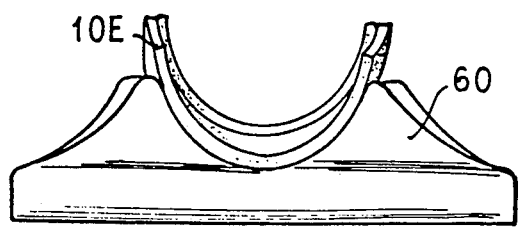
FIG. 12 is an end view of the device shown in FIG. 11.

A further use for the brace shell support is shown in FIGS. 10 through 12 in which the shell 10E is placed in a contoured pillow 60 so that the shell 10E will be held in a fixed orientation relative to the pillow such that the brace will be securely held against the user's head and neck area when user is in a reclining or semi-reclining position. Although FIG. 10 shows two lateral pad strips 62 placed within the shell body, any of the padding arrangements described above could be utilized in this configuration.

This use of the brace shell 10E again provides support for the head and neck area when the user is in a reclining or semi-reclining position for a period of time without the confinement and awkwardness of the foam collar to hold the brace in place.

FIG. 13 illustrates an improved cervical/occipital support or shell 70 which, similar to the neck brace 10 described with respect to FIGS. 1-12 is worn on the neck of a user U and is held in close conformity with the posterior region of the user's neck, shoulders and lower skull. As seen in FIG. 16, the support 70, when viewed from below (or above), is generally U-shaped having an inner-edge or an inner-surface 72 which conforms generally with a posterior neck area of the user. The support 70 is contoured to provide distinct surface areas for contact with specific anatomical regions of the human body.

As seen in FIGS. 13 and 18, an upper area 74 provides support and cradles the occiput between the ears. This area also prevents hyper-extension at the atlanto-occipital junction. A second central area 76 surrounds and contacts the posterior lateral neck area. A third lower area 78 contacts and rests on the base of the neck and suprascapular region of the user's shoulders and continues anteriorly to rest on the clavicles. Transition zones or contours 80 and 82 occur between the first and second areas and the second and third areas respectively.

The support 70 is constructed of a semi-rigid material such as polymeric plastic material and the various contours 80, 82 of the support not only give the necessary support but also increase the rigidity of the support 10.

Additional contours 83, 84 are provided closely adjacent the top and bottom edges of the support 70 to further increase the rigidity. Contour 84 prevents the bottom edge of the support 10 from turning up The rigidity of the brace is not so great as to totally prevent any motion. The brace does have some resiliency which allows forceful movement when a position change will give relief to the user.

An improved means for retaining the support 70 on the user's neck is illustrated in FIGS. 13-18 which includes an encircling strap 85 secured by an appropriate retaining means 86 such as a rivet to the support which has at its forward ends a pad area 88 comprising the hook portion of a hook and pile fastening system. The hook pad area 88 may be fastened to the support 70 such as by stitching or by an adhesive. A removable strap 90 which can be made of an elastic material has a section 92 of pile or loop material of the hook and pile fastening system attached at either end of the strap which is engagable with the hook portion 88. In this manner, there is infinitely continuous adjustment of the strap 90 relative to the support 70.

A throat pad 94, shown in greater detail in FIG. 17, is carried on the strap 90 by means of a pair of slits 96, 97 formed in the pad through which the strap 90 passes. The pad is to be positioned at the front of the user's neck to overlie the user's larengeal prominence and a central portion 98 of the pad is relieved to provide clearance for the larengeal prominence.

The support 70 has forwardly extending side wings or extensions 100 which extend forwardly of the user's ears, almost to the front of the user's neck but are short of providing a complete encircling of the user's neck. As seen in FIG. 14, a very front end 102 of the wings 100 is curved outwardly at 102 which further assists in holding the throat pad 94 away from the user's larynegeal prominence. Thus, the support 70 can be held against the user's head and neck quite securely without resulting in excessive pressure or discomfort to the user by engagement with the user's larengeal prominence.

The extensions 100 can also be provided with markings and trim lines 103 corresponding, for example, to shirt sizes so that the brace may be altered to provide a customized fit for additional comfort to the user.

As seen in FIG. 15, a further improvement includes the provision of trim lines 104, 105 on the rear portion of the support at the lower area 78. These trim lines are included to allow the person fitting the support 70 on the patient to make the support fit more closely in the event that the upper spinal area of the patient is more pronounced especially in patients who have a postural deformity such as elderly arthritic or kyphotic patients. It should also be understood that it is within the scope of the present invention to provide a special model which is made with the trim area already removed from the support 70 as shown in FIG. 15A which provide a recessed portion arranged to overlie the lower cervical and upper thoracic spinal area of the user to provide a clearance for that spinal area.

FIGS. 19-22 illustrate another means for retaining the support 70 on the neck of the user which includes a chin support shell 106 which includes a pocket area 108 for receiving the user's chin, including a cut-out or removed area 110 to provide clearance for the front of the user's chin to prevent jaw discomfort particularly at the temporal-mandibular joint. A bottom end 112 of the chin support shell is arranged to rest on the user's upper chest to provide additional restraint against flexion of the user's neck.

The chin support shell 106 has a strap 114 secured thereto by appropriate fastening means 116 such as a rivet and has a pad section 118 at either end of the strap 114 which is a loop portion of a fastening system which is secured to the hook portion 88 of the fastening system attached to the support 70. Thus, the position of the chin support shell 106 is infinitely and continuously adjustable.

Figure 23:
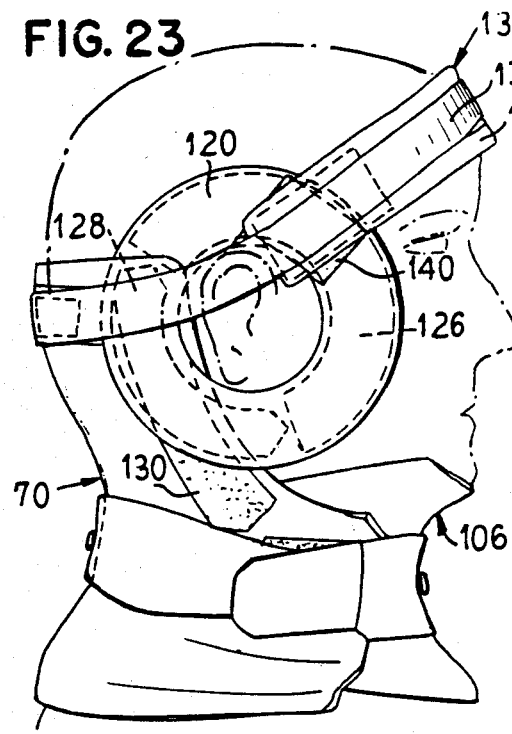
FIG. 23 is a side elevational view of the head and neck support and chin support of FIG. 19 and further including attached ear protectors and head band.
Figure 24:
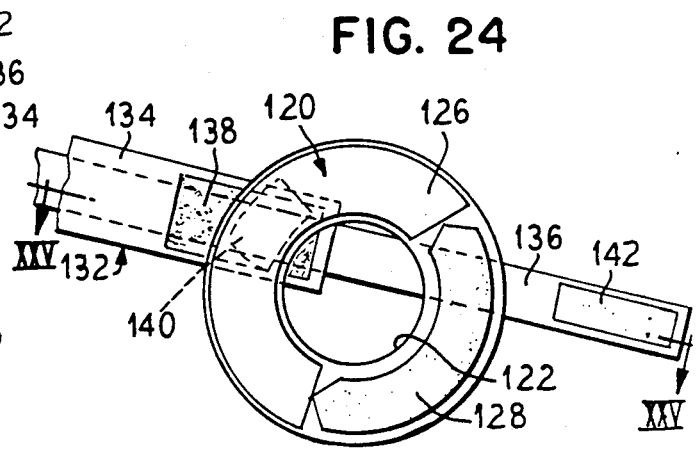
FIG. 24 is a side elevational view of the ear protector shown in FIG. 23.
Figure 25:
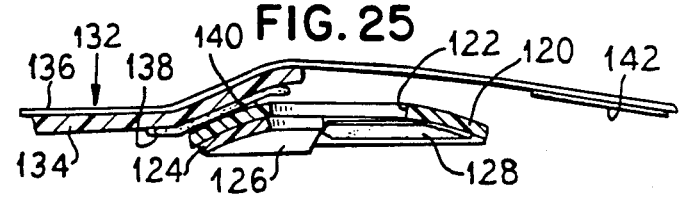
FIG. 25 is a top sectional view of the ear protector taken generally along the lines XXV—XXV of FIG. 24.

FIGS. 23-25 illustrate an additional attachment for the support 70 which includes a pair of ear protectors 120 which are generally ring shaped members having a central opening 122 sized to receive a human ear. A portion of an interior surface 124 of the ear protector 120 may be covered with a cushioning material 126 such as T-foam, CONFORM ® foam or a polymeric plastic, described above, to provide a self adjusting pad for close engagement of the ear protector 120 against the side of the user's head. The thickness of the pad 126 can be selected to provide the necessary protection of the ear as well as the conforming function. If needed, a second layer of foam could be utilized. Another portion of the interior surface 124 of the ear protector 120 has a pad 128 of hook material which is engagable with a pad 130 of loop material which has been fastened to the exterior surface of the support at the area adjacent the ear. In this manner, the ear protectors 120 can be placed over the patient's ears and attached to the support 70 in an infinitely variable number of positions to provide for accurate placement and positioning of the ear protector to provide maximum comfort and support for the posterior portion of the mandible.

The use of the ear protectors is especially helpful in the case of accident victims being transported from the scene of an accident to a hospital or other health care facility in that it is customary practice to immobolize the patient by placing the patient's head between sand bags or other relatively immobile restraining devices. Generally, this causes a painful pressure against the patient's ears which the use of the ear protectors will prevent. Thus, the sand bags will engage against the ear protectors to restrain the head from movement, but the ears will be free from compression due to the openings 122 in the protectors. The use of the internal pads 126 will provide a gentle but firm engagement of the protector against the user's head. The ear pads may also be useful where sand bags or other similar restraining devices are utilized such as during the taking of x-ray head is restrained in the hospital bed. It is advantageous that the ear protectors are easily removable so that they can be removed when not required.

A head band 132 may also be used to hold the top end 74 of the support tightly against the occiput and also to ensure that the ear protectors 120 are held in place. The head band 132 includes a central portion 134 which may be made of a foam or absorbent material to engage the user's forehead. An elastic strap 136 is attached to the central portion 134. An interior surface of the central portion 134 has at each end a pad 138 of loop material which is adjustably engagable with a pad 140 of hook material attached to the exterior of the ear protectors 120. In this fashion, the head band 132 is attached to the ear protectors.

The elastic strap 136 has a pad 142 of hook material attached at either end to adjustably engage the pad 130 of pile material attached to the exterior surface of the support 70. In this fashion, the head band 132 is attached to the support. The attachment of the head band 132 to the support 70 occurs at the top portions 74 and generally at the lateral posterior region of the support 70 such that the support will be held closely adjacent to the user's occiput. The head band 132 can be used with or without using the ear protectors 120 (FIG. 26).

Figure 26:
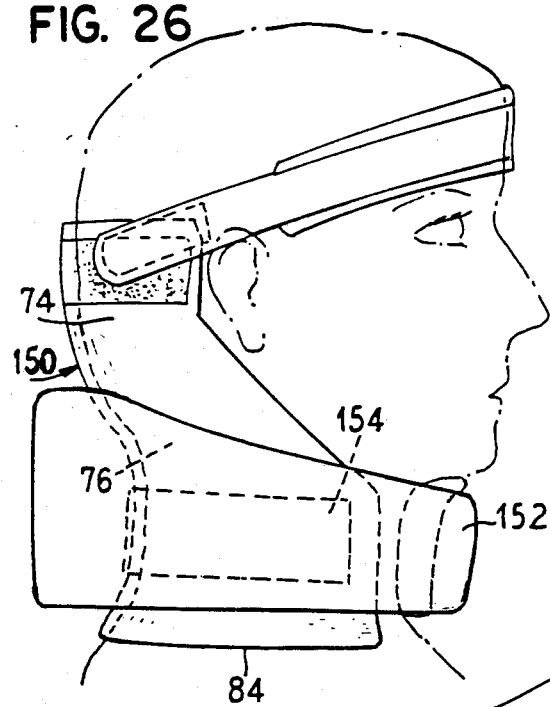
FIG. 26 is a side elevational view of an alternative embodiment of the neck brace held on by an encircling collar and head band.
Figure 27:
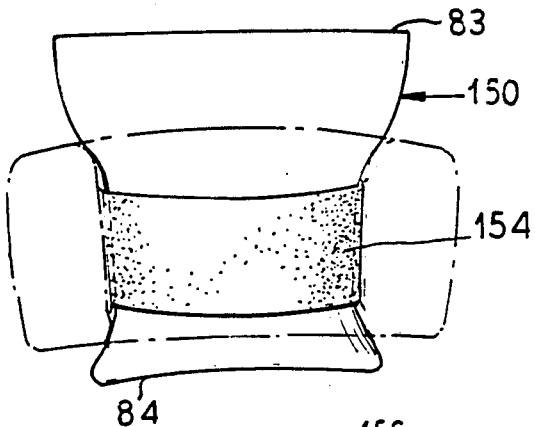
FIG. 27 is a rear elevational view of the brace shown in FIG. 26.
Figure 28:
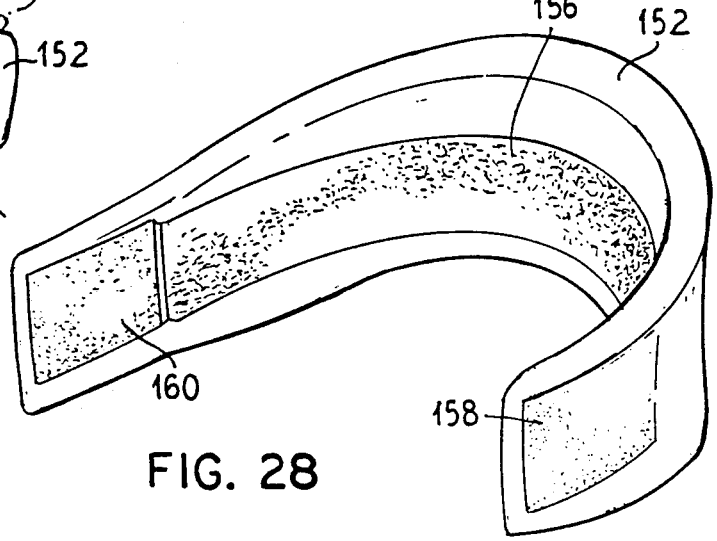
FIG. 28 is a perspective view of the retaining collar used in FIG. 26.

An alternate embodiment of the support is shown in FIGS. 26 and 27 at 150. This embodiment is virtually identical to the support 70 described with respect to FIGS. 13-25, in the upper two thirds of that support, in that the embodiment of FIGS. 26 and 27 includes the upper region 74 and central region 76, but the lower region 78 has been reduced by trimming along contour 84. To hold the modified support 150 on the user's head and neck area, an encircling collar 152 is utilized. The support 150 may have a pad 154 of hook material secured thereto on an exterior surface and the collar 152 has a pad 156 of loop material on an interior surface to securely, but adjustably hold the collar 152 on the support 150. An additional hook pad 158 and loop pad 160 of material may be attached to ends of the collar 152 to provide for an adjustable positioning or tightening of the collar around the user's neck. The encircling collar attaching means illustrated in FIGS. 26-28 can also be used for the previously described embodiments of the head and neck support.

Figure 29:
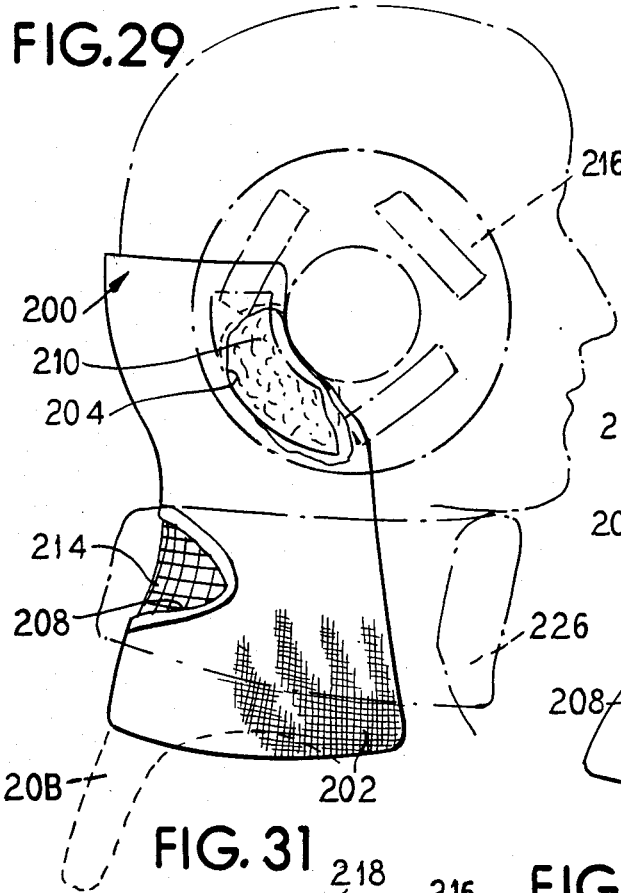
FIG. 29 is a side elevational view of an alternative embodiment of a neck brace with an attachable ear pad and a removable cloth cover embodying the principles of the present invention.
Figure 30:
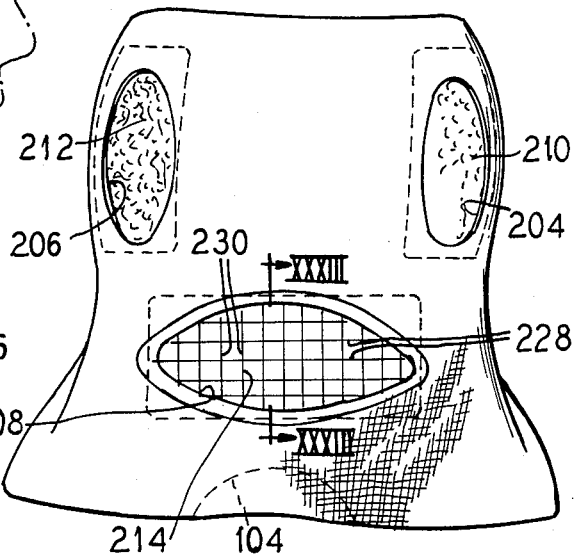
FIG. 30 is a rear view of the neck brace illustrated in FIG. 29.

In FIGS. 29 and 30 there is illustrated a posterior shell 200 which has an exterior cloth cover 202 which may be fabricated of cotton for example to virtually completely enclose the shell 200, but which has a pair of side openings to 204, 206 and a rear opening 208 to expose pads 210, 212 of loop or pile material and a pad 214 of hook material of a hook and loop fastening system. The cover 202 can be applied and removed through opening 208.

As illustrated in phantom in FIG. 29, the side pile pads 210, 212 can be utilized to provide an attachment point for an ear protector ring 216 similar to the protector 120 described above. Such an ear protector is shown in greater detail in FIGS. 31-32 which illustrate that the protector is a circular member having a central opening 218 to permit viewing of ear for the possibility of bleeding or spinal fluid leakage and post head trauma. The interior side of the protector is lined with a soft foam material 220 for at least the portion of the ear protector which will lie against the patient's face. The sector which lies over the shell 200 has a hook pad 222 to engage with the loop pad 210 or 212 on the brace 200. The exterior portion of the protector 216 is formed of a more rigid material and includes either a plurality of hook pads 224 or a continuous annular hook pad for engagement with a head band as shown in FIGS. 23-25 and described above and/or with a modified overlying posterior shell such as shown in FIGS. 39-40 and described below.

Also shown in phantom in FIG. 29 as an optional extension of the shell 200 is a lower area 20B corresponding to the area shown in FIG. 7 above.

The posterior shell 200 of FIGS. 29 and 30 may be secured on the patient's neck by means of a foam collar 226 which may attach to the hook pad 214 at the rear of the shell. The foam collar can be adjusted in place by reference to various horizontal lines 228 or vertical lines 230 on the hook pad 214 to provide different degrees of flexion if moved upwardly or extension if moved downwardly and different degrees of tightness. This is described in greater detail below with respect to FIG. 41. The trim line 104 is shown in phantom in FIG. 30, which is discussed in connection with FIGS. 15, 15A above.

An improved anterior shell 240 is illustrated in FIGS. 34-37 which also can be provided with an exterior cloth covering 242 which covers the interior and exterior of the anterior shell and which is provided with various side openings 244 and an anterior opening 245 to provide access to attachment pads 246, 248. The cover can be applied and removed for cleaning through anterior opening 245.

The anterior shell includes a chin cup area 250 which is open to the front to permit the user's jaw to protrude through the front opening. The anterior shell includes raised sidewall portions 254 which extend upwardly and inwardly at depressed contour line 255 to positively grasp the mandible to resiliently control lateral movement of the jaw. The chin cup may include a soft pad lining 252 and the thickness of the pad elevates the mandible off the shell. The jaw is supported at the front lower part of the mandible and the posterior jaw line is left relatively unsupported to permit adequate blood flow to the face and head through facial arteries which extend along the jaw line.

Air holes 256 are provided at various locations in the anterior shell and are preferably formed as triangles in the portions of the shell which includes a hook or loop pad so that the rigidity of the shell is not detrimentally affected by the addition of the air holes 256. Similar air holes may be provided in shell 200. Trim lines 257 may be provided to permit an area to be trimmed out for a tracheotomy in the event of a medical emergency.

The rigidity of the anterior shell can be enhanced without an external strut or internal rigid materials by the addition of molded contours 258, 260. The vertical contour 258 extends from near a bottom central portion of the shell midway up the front of the shell where it meets with a curved semi-circular contour 260 extending upwardly from a relief area 261 on a lower edge of the shell which overlies the clavicle. These contours 258, 260 provide an increased rigidity for the shell while permitting it to remain somewhat flexible which, as has been described above, is desirable.

A foam cushion 262 can be provided at a lower front portion of the shell in the contour region to overlie the patient's chest to disperse pressure from the anterior shell against the chest providing some measure of chest pressure relief.

The anterior shell 240 can be secured in place in an overlying relationship to a posterior shell 264 by means of a strap 266 which is shown in FIGS. 37 and 38. The strap preferably is formed in five sections, the two end sections 268, 270 being hook pads of a hook and pile fastening system which are engagable with side loop pads 246 on the anterior shell 240. An exterior side of the end sections 268, 270 preferably includes vertical lines 272 which can be used in conjunction with indicia markings such as a vertical line or pointers 278 on the anterior shell side pad 246 to provide a measurement and aligning feature similar to that described with respect to FIG. 18 above.

A central portion 280 of this strap preferably is a pad of loop material which can removably attach to a hook pad such as pad 214 on the shell 200 illustrated in FIG. 29.

Finally, there are two sections 282, 284 which extend between the central portion 280 and the end portions 268, 272 which are preferably of an elastic material which will ensure a resilient holding of the anterior shell over the posterior shell by the strap.

An adjustable collar such as plastic collar 286 (shown in phantom in FIG. 37) or a foam collar 226 (shown in phantom in FIG. 29) can be used to provide additional rigidity and support for the shells.

FIGS. 39 and 40 illustrate an alternative embodiment of a posterior shell 290 which is similar to the shells described above, and can be used as a single posterior shell, but in addition it includes an integrally formed ear covering portion 292 which can either be formed as an ear protector of the type described above with respect to FIGS. 23-25 and FIGS. 31-32 or, it can be a support area for receiving an ear protector ring such as that illustrated in FIGS. 31-32.

Figure 31:
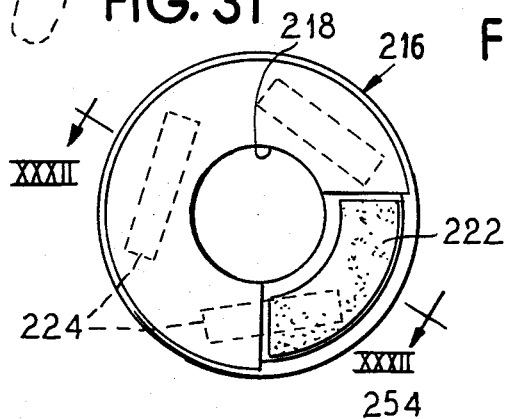
FIG. 31 is a side elevational view of the ear pad depicted in phantom in FIG. 29.
Figure 32:
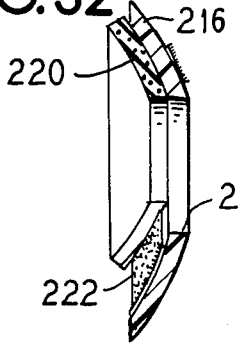
FIG. 32 is a side sectional view taken generally along the line XXXII—XXXII of FIG. 31.
Figure 33:
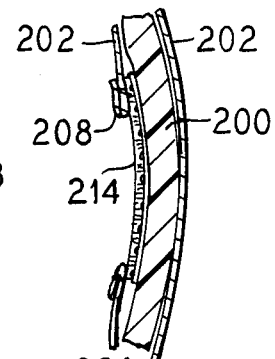
FIG. 33 is a partial sectional view taken generally along the line XXXIII—XXXIII of FIG. 30.
Figure 34:
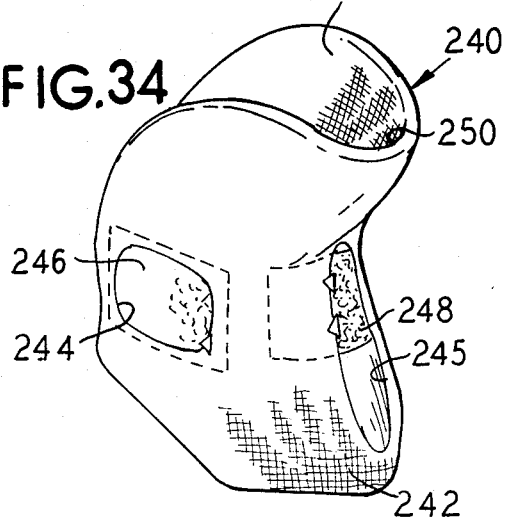
FIG. 34 is a perspective view of an alternative embodiment of an anterior shell with a removable cloth cover which can be used with the posterior shell of FIG. 29.
Figure 35:
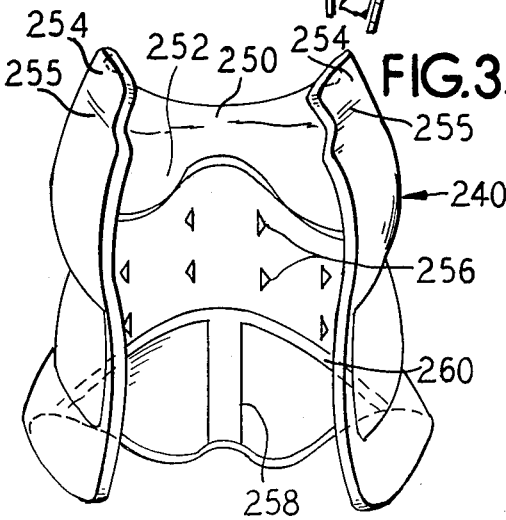
FIG. 35 is a rear elevational view of the anterior shell of FIG. 34.

The interior surface of the posterior shell 290, in the region of the ear protector portion 292, may be provided with loop material to engage the hook pads 224 of the ear protector 216 of FIGS. 31-32 to securely hold the ear pad in place. The shell 290 comprises a preformed U-shaped shell fabricated of a resilient material contoured to overlie the occipital bone, lower parietal bone and a major part of the temporal bone including the zygoma vertically and posterolaterally and neck posterolaterally to the base of the neck (and optionally extending downwardly into the inter scapular area), having an integrally formed forward upper edge 293 which extends anterior of and superior to the user's ears and includes an adequate opening 294 with generous clearance to allow emergence of the user's ears. The borders of the opening 294 have sufficient material to support and cushion the engaged areas of the skull and posterior mandible, thereby limiting lateral bending and rotation of the head and neck. The ear protector portion 292 may have a substantially vertical trim line 292A at an anterior portion of the ear protector which would permit removal of a portion of the shell at that area if needed for particular facial characteristics of the patient.

The shell 290 may also be an enlarged shell which would overlie a smaller shell such as shell 70 shown in FIG. 23 so that the ear protector 120 would be sandwiched between the inner shell 70 and the outer shell 290. The outer shell would provide increased rigidity as is described above with respect to FIGS. 8 and 9.

It can clearly be seen in FIG. 40 that the ear protector engages the zygomatic arch Z of the patient and is spaced away from the temporal-mandibular joint T so that a lower portion of the ear protector will support the posterior mandible below the temporal-mandibular joint T, the ear protector bridging and being spaced from the joint T.

As a duplicate exterior shell, the shell 290 would overlie both a posterior shell such as shell 264 shown in FIG. 37, and the anterior shell 240 and can be held in place by a combination of the encircling strap 266 as well as a multiply adjustable head band 296. Pads of loop material 298 can be provided at a posterior portion of the shell where it cradles the occiput and which can engage with a hook pad 299 of an upper leg 300 of an elastic head band connector strap 302. Lateral loop pads 304 overlying the neck area can be engaged by a hook pad 306 on a lower leg 308 of the head band strap 302 at each side of the head. By providing a two leg strap attachment, the head can be held in various degrees of flexion or extension as is required due to the particular injury involved. Head band leg strap 308 can be selectively attached via pad 306 anywhere along pad 304 as indicated by arrow 309 and position of leg strap 308 in phantom to achieve desired support. An additional connection can be made by a hook and loop fastening connection at 310 at a top forward position on the ear covering portion 292 and adjacent to an adjusting buckle 311 for the strap. Each of the leg straps 300, 308 may also have an adjusting buckle 311A, 311B to provide the desired tension to each leg of the head band 296. This provides additional stability of the head band 296.

It is within the scope of this invention to utilize duplicate shells of different densities and dimensions as previously described in my U.S. Pat. No. 4,562,833 relating to the posterior shell. The shells may be temporarily or permanently joined.

This exterior shell 290 may be formed of a more rigid plastic material such as polyethylene and if so can be contoured as shown in full lines in FIGS. 39 and 40 with a top rear portion recessed downwardly to a top rear wall at 312. If the posterior shell 290 is formed from the same polymeric plastic material as the other shells, then it is preferable for the top contour of the shell to continue at the same elevation as the top of the ear covering portion 292 to have a top rear wall at 314 to provide additional rigidity and stability to the rear shell thereby limiting lateral bending and rotation of head and neck as well as flexion and extension.

The shell may also be formed of a sandwich or laminated material having a semi-rigid plastic interior material and a semi-rigid softer exterior material.

Figure 41:
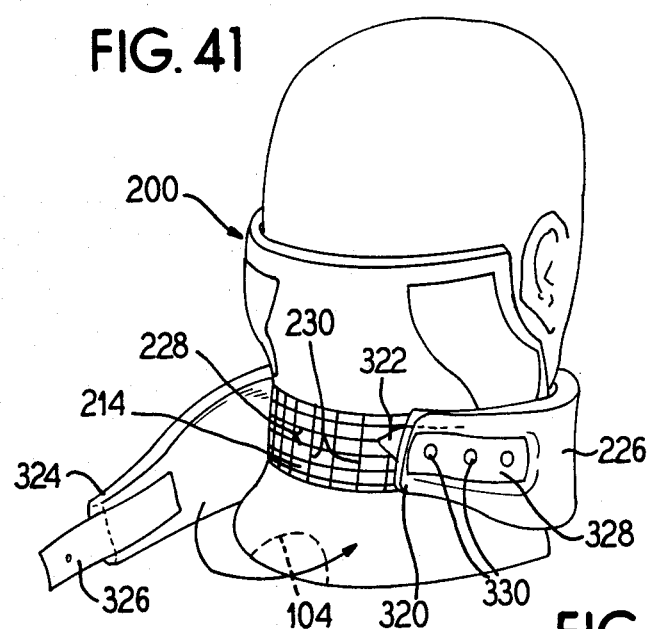
FIG. 41 is a rear perspective view of an attachment arrangement for a posterior shell with a foam collar.
Figure 42:
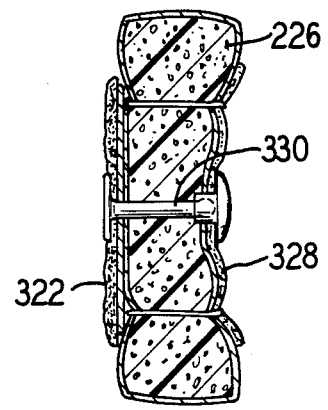
FIG. 42 is a sectional view through the foam collar illustrating a riveted connection.
Figure 43:
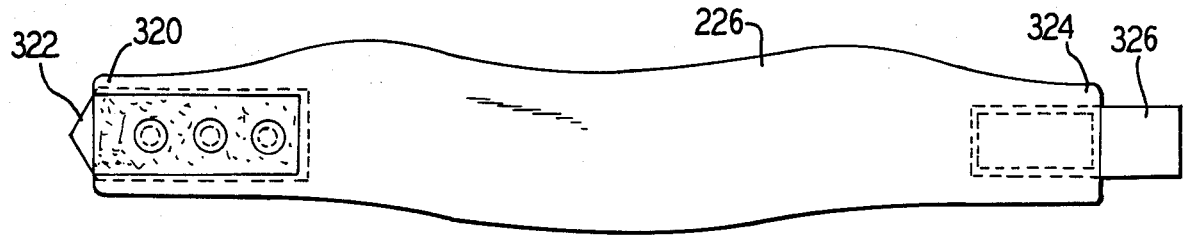
FIG. 43 is an elevational view of the foam collar of FIGS. 41 and 42.
Figure 42A:
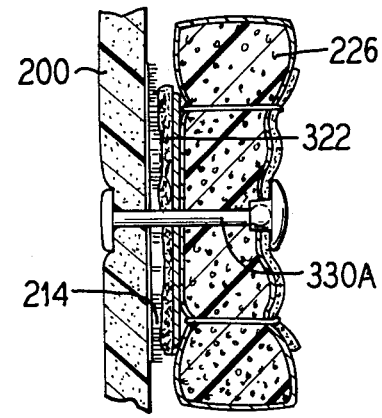
FIG. 42A is a sectional view through the foam collar and shell illustrating a riveted connection.

In FIG. 41 there is illustrated the manner of securing a posterior shell such as shell 200 to the patient by use of the foam collar 226 which was alluded to above. The foam collar 226 is shown in more detail in FIGS. 42 and 43 and it is seen that a first end 320 includes a permanently attached loop material pointer 322 which can be aligned by medical personnel to the horizontal 228 and vertical 230 lines on the rear hook pad 214 so that the proper degree of flexion or extension can be provided. A second end 324 of the collar 226 includes a strap 326 having an interior surface lined with loop material to engage with a pad 328 of hook material attached to the first end 320. FIG. 42 illustrates a section through the foam collar 226 and in particular through the first end 320 illustrating a riveted connection of the hook pad 328 and pointer material 322 which may be a loop pad which can attach to the hook pad 214 on the shell. Rivets 330 are preferably used. As is the case with all of the pile and hook fastening pads, a manufacturer may want to reverse the hook and pile positions from those described herein, which would not affect the functioning of the device. A semi-removable type of rivet 330A may also be used so that the medical personnel can actually rivet the collar to the shell 200 as shown in FIG. 42A to hold a desired placement of the collar relative to the shell 200 between prescriptions or fittings. In this manner, the patient would be unable to readjust the collar to an inappropriate location.

Figure 44:
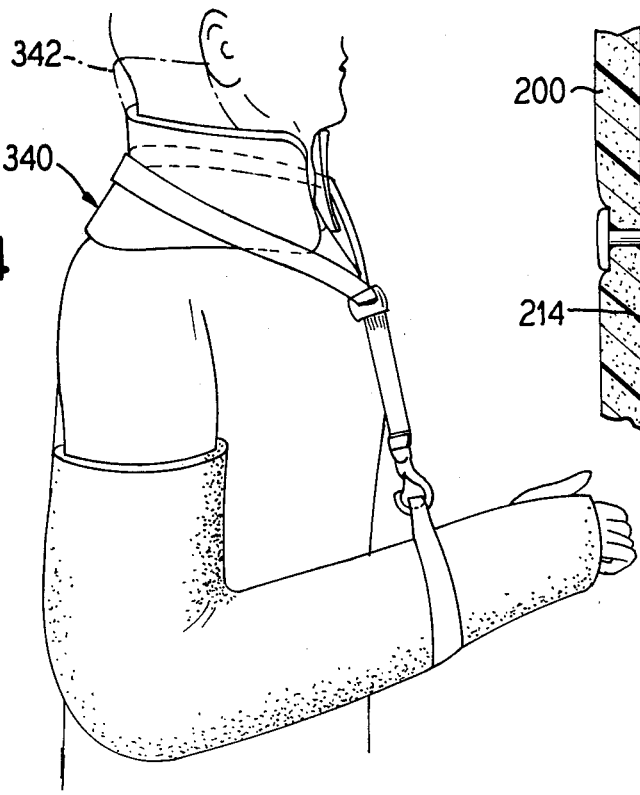
FIG. 44 is a perspective view illustrating an additional use for the neck brace.

FIG. 44 illustrates an additional use for posterior shell 340 which would be as a force spreading means such as when the patient needs to support an injured arm. If the head does not require additional support due to an injury, a superior portion 342 of the type of shells described above can be removed as is illustrated in phantom so that the shell 340 does not extend upwardly as far as the user's head.

As is apparent from the foregoing specification, the invention is susceptible of being embodied with various alterations and modifications which may differ particularly from those that have been described in the preceeding specification and description. It should be understood that I wish to embody within the scope of the patent warranted hereon all such modifications as reasonably and properly come within the scope of my contribution to the art.

I claim as my invention:

1. A head and neck support comprising a semi-rigid preformed U-shaped anterior chin supporting shell fabricated of a resilient material, said shell having a chin support area with a front opening, a lower front edge engagable against the user's chest and preformed vertical and semi-circular contours to enhance the rigidity of the shell, said vertical contour extends upwardly from a central portion of said chest engaging front edge, and said semi-circular curved contour curves upwardly from opposing lateral sides of said chest engaging front edge.

2. A head and neck support according to claim 1, wherein said contours merge at a front central point on said shell below said chin support area.

3. A head and neck support according to claim 1, including a removable cloth cover for said anterior shell.

4. A head and neck support according to claim 1, wherein said shell has a top edge which extends above the user's mandible and curves vertically inwardly at a depressed contour to positively, yet resiliently engage the mandible of the user.

5. A head and neck support according to claim 1, wherein said chin support area includes a chin engaging pad of a thickness to support a front portion of the mandible while spacing a rear portion of the mandible from the anterior shell.

6. A head and neck support according to claim 1, including retaining means engagable with said shell to hold said shell against a user's head and neck and wherein said cover includes openings therein to permit said retaining means to engage said shell.

7. A cervical and occipital support for use in supporting a user's head and neck, comprising:
   a semi-rigid preformed U-shaped posterior shell fabricated of a solid, resilient material, contoured to fit the occipital bone area of the skull vertically and posterolaterally between attachment locations of the ears, and the neck posterolaterally at least to the base of the neck;
   a semi-rigid preformed U-shaped anterior chin supporting shell fabricated of a resilient material;
   said anterior shell having a chin support area with a front opening, a lower front edge engageable against the user's chest and preformed vertical and semi-circular contours to enhance the rigidity of the shell; and
   a retaining means selectively attachable to said shells to retain said shells against the head and neck of said user.

8. A cervical and occipital support according to claim 7, wherein said anterior shell includes attachment areas for removably securing said retaining means to said anterior shell.

9. A cervical and occipital support according to claim 1, wherein said anterior shell includes a chest engaging foam cushion pad at said lower front edge.

10. A cervical and occipital support according to claim 7, including a removable cloth cover for at least one of said posterior and anterior shells.

11. A cervical and occipital support according to claim 7, wherein said posterior shell includes attachment areas for removably securing said retaining means to said posterior shell, said retaining means comprising a neck encircling member having a tab at one end engagable with said attachment area and said attachment area having markings thereon permitting said member to be selectively aligned with said shell.

12. A cervical and occipital support according to claim 7, wherein said anterior shell includes air openings therethrough.

13. A cervical and occipital support according to claim 12, wherein said openings are triangular in shape.

14. A cervical and occipital support according to claim 7, wherein said anterior and posterior shells are reinforced with duplicate shells in a nested arrangement.

15. A cervical and occipital support according to claim 14, wherein said duplicate shells have a different density than the shells with which they nest.

16. A head and neck support comprising a first semi-rigid preformed U-shaped shell fabricated of a resilient material contoured to overlie the occipital bone, lower parietal bone and a major part of the temporal bone including the zygoma vertically and posterolaterally and the neck posterolaterally at least to the base of the neck having an integrally formed forward upper edge which extends anterior of and superior to a user's ears and including an adequate opening with generous clearance to allow emergence of the user's ears, borders of said opening having enough material to sufficiently pad for support the engaged areas of the skull thereby limiting lateral bending and rotation of the head and neck as well as flexion and extension.

17. A head and neck support according to claim 16, including a semi-rigid preformed U-shaped anterior chin supporting shell fabricated of a resilient material.

18. A head and neck support according to claim 16, including separate ear protector rings removably attached to an interior surface of said shell at said forward upper edge, said rings having an interior opening aligned with said openings in said shell.

19. A head and neck support according to claim 16, including a retaining means for holding said shell against the user's head and neck.

20. A head and neck support according to claim 19, wherein said retaining means comprises an adjustable head band removably attached to said shell and a neck encircling retaining member.

21. A head and neck support according to claim 16, including a second semi-rigid preformed U-shaped shell fabricated of a resilient material contoured and sized to nest within said first shell to fit the occipital bone, lower parietal bone and a major part of the temporal bone including the zygoma vertically and posterolaterally and neck posterolaterally at least to the base of the neck.

22. A head and neck support according to claim 21, including ear protector rings removably sandwiched between said second shell and said first shell, said rings having an interior opening aligned with said openings in said first shell.

* * * * *